US008815262B2

(12) United States Patent
Tsujihata

(10) Patent No.: US 8,815,262 B2
(45) Date of Patent: Aug. 26, 2014

(54) PHARMACEUTICAL COMPOSITION AND PREPARATION FOR ORAL ADMINISTRATION

(75) Inventor: Shigetomo Tsujihata, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/575,547

(22) PCT Filed: Jan. 27, 2011

(86) PCT No.: PCT/JP2011/051674
§ 371 (c)(1),
(2), (4) Date: Jul. 26, 2012

(87) PCT Pub. No.: WO2011/093416
PCT Pub. Date: Aug. 4, 2011

(65) Prior Publication Data
US 2012/0315306 A1    Dec. 13, 2012

(30) Foreign Application Priority Data
Jan. 29, 2010 (JP) .................................. 2010-19723

(51) Int. Cl.
*A61K 31/337* (2006.01)
*A61L 31/00* (2006.01)

(52) U.S. Cl.
CPC ...................................... *A61L 31/00* (2013.01)
USPC ............................ 424/400; 424/401; 522/181

(58) Field of Classification Search
CPC .............................. A61L 31/337; A61L 31/10
USPC .................................. 424/400, 401; 522/182
See application file for complete search history.

(56) References Cited

U.S. PATENT DOCUMENTS

| | | | |
|---|---|---|---|
| 5,118,528 A | 6/1992 | Fessi et al. | |
| 5,133,908 A | 7/1992 | Stainmesse et al. | |
| 6,214,957 B1 | 4/2001 | Shiino et al. | |
| 2006/0255323 A1 | 11/2006 | Seki et al. | |

FOREIGN PATENT DOCUMENTS

| | | | |
|---|---|---|---|
| JP | 63-240936 A | 10/1988 | |
| JP | 3-39309 A | 2/1991 | |
| JP | 10-109029 A | 4/1998 | |
| JP | 2003-137816 A | 5/2003 | |
| JP | 2007-126423 A | 5/2007 | |
| WO | 2005/051511 A1 | 6/2005 | |

OTHER PUBLICATIONS

Konno et al.; Title: Enhanced solubility of paclitaxel using water-soluble and biocompatible 2-methacryloyloxyethyl phosphorylcholine polymers. Journal of Biomedical Materials Research Part A, vol. 65A, Issue 2, pp. 209-214, published on May 1, 2003 by Wiley.*
Konno et al., Title: Enhanced solubility of paclitaxel using water-soluble drug an dbiocompatible is 2-methacryloyloxyethyl phosphorylcholine polymers; J. Biomed. Mater. Res. part A, 2003, pp. 209-214, vol. 65, No. 2, published by Wiley Periodicals, Inc.*
Win et al., Title: Effects of particle size and surface coating on cellular uptake of polymeric nanoparticles for oral delivery of anticancer drugs; Biomaterials; vol. 26, Issue 15, May 2005, pp. 2713-2722), published by Elsevier.*
Written Opinion, mailed Mar. 1, 2011, issued in corresponding International Application No. PCT/JP2011/051674, 10 pages in English and Japanese.
Tomohiro Konno et al., "Enhanced solubility of paclitaxel using water-soluble and biocompatible 2-methacryloyloxyethyl phosphorycholine polymers", J Biomed Mater Res A, 2003, pp. 209-214, vol. 65, No. 2.
K. Sakaguchi et al., "Chapter 10 Development of Solubilizer using Water-Soluble Phospholipid Polymer", Nano-Bio Engineering Material, Mar. 10, 2004, pp. 255-261.
International Search Report for PCT/JP2011/051674 dated Mar. 1, 2011, 7 pages in Japanese and English, only English portion has been considered.
Office Action dated Aug. 13, 2013 in Chinese Application No. 201180007425.
Office Action dated Mar. 25, 2014 in Japanese Application No. 2011-551917.
Wada et al, Efficacy of an MPC-BMA Co-polymer as a Nanotransporter for Paclitaxel, Anticancer Research, vol. 27, pp. 1431-1436, Dec. 31, 2007.
Extended European Search Report dated Mar. 19, 2014 in European Application No. 11 73 7127.8.
Office Action dated May 4, 2014 in Chinese Application No. 201180007425.
Japanese Office Action dated Jun. 10, 2014, issued in corresponding Japanese Patent Application 2011-551917.

* cited by examiner

*Primary Examiner* — Richard Schnizer
*Assistant Examiner* — Yanzhi Zhang
(74) *Attorney, Agent, or Firm* — Sughrue Mion, PLLC

(57) ABSTRACT

A pharmaceutical composition including drug-containing nanoparticles having an average particle diameter of from 10 nm to 150 nm, the pharmaceutical composition being obtained by mixing water with a poorly water soluble drug-containing, water miscible solution that contains a poorly water soluble drug having a water solubility of 50 μg/mL or less, a water soluble copolymer having a repeating unit represented by the following Formula (1), and a water miscible miscible solvent, wherein in Formula (1), n:m is within a range of from 0.25:0.75 to 0.95:0.05, R represents an alkyl group which may have a substituent, $R^1$ and $R^2$ each independently represent a hydrogen atom or a methyl group, and Me represents a methyl group; and a preparation for oral administration, which includes the pharmaceutical composition.

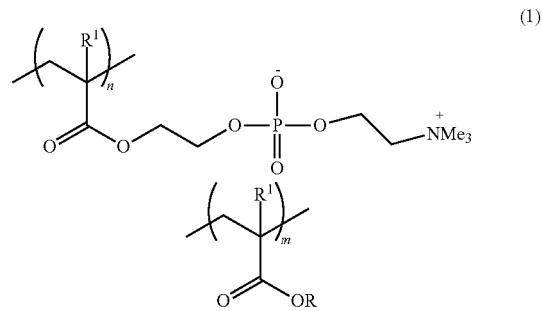

(1)

12 Claims, No Drawings

PHARMACEUTICAL COMPOSITION AND PREPARATION FOR ORAL ADMINISTRATION

CROSS REFERENCE TO RELATED APPLICATIONS

This application is a National Stage of International Application No. PCT/JP2011/051674 filed Jan. 27, 2011, claiming priority based on Japanese Patent Application No. 2010-019723 filed Jan. 29, 2010, the contents of all of which are incorporated herein by reference in their entirety.

TECHNICAL FIELD

The present invention relates to a pharmaceutical composition and a preparation for oral administration.

BACKGROUND ART

Currently, compounds having various chemical structures hold promise as medicines such as anticancer drugs or antiviral drugs, and are actually used for clinical treatment. However, among these, poorly water soluble drugs are known that have an extremely low solubility with respect to water despite having an extremely excellent pharmacological effect. There are cases in which, with respect to these poorly water soluble drugs, the administration method is restricted or clinical application in an appropriate concentration is difficult, and, in such a case, sufficient therapeutic effects may not be demonstrated.

For example, paclitaxel has excellent pharmacological activity as an anticancer drug and has recently been widely clinically used; however, in present circumstances, since the solubility of paclitaxel with respect to water is extremely low (the degree of solubility is 6 μg/mL or less), the administration method is restricted, and sufficient therapeutic effects are not obtained. Usually, when administering paclitaxel to cancer patients, paclitaxel is dissolved in physiological saline using polyoxyethylene castor oil and dehydrated ethanol as solubilizing agents, and then the solution thus obtained is administered by intravenous drip infusion over 3 hours.

Further, cases have been reported in which the above polyoxyethylene castor oil used as a solubilizing agent exhibits very serious side effects such as anaphylactic shock. Since surfactants are generally used in order to solubilize poorly water soluble drugs, the occurrence of side effects due to surfactants, as described above, should be avoided if at all possible. Therefore, not only reduction of the side effects of intravenous drip injection, but also improvement of the administration method is required, from the viewpoint of the quality of life (QOL) of the patients.

Meanwhile, in the case of orally administering paclitaxel, since the degree of solubility of paclitaxel is low, and further, since paclitaxel is discharged by P-glycoprotein in gastrointestinal epithelia, it is known that the bioavailability thereof is extremely low, being in the region 4% or less. Therefore, with regard to paclitaxel, further improvement has been deemed necessary in order to obtain a preparation for oral administration, which is most desirable from the viewpoint of enhancement of QOL.

In many types of poorly water soluble drugs other than paclitaxel as well, problems similar to those of paclitaxel are in evidence. Accordingly, enhancement of the solubility of poorly water soluble drugs with respect to water and improvement of the bioabsorption ratio are expected to make it possible to realize various kinds of drug therapy associated with poorly water soluble drugs.

From one such viewpoint, a copolymer (hereinafter, referred to as "Poly(MPC-co-BMA)") having excellent biocompatibility, the copolymer being obtained by using 2-methacryloyloxy ethyl phosphoryl choline (hereinafter, referred to as "MPC"), which is a monomer having a phospholipid polar group, and n-butyl methacrylate (hereinafter, referred to as "BMA"), which is a hydrophobic monomer, has been developed (see, for example, Japanese Patent Application Laid-Open (JP-A) No. 3-3939) and has been commercialized under the trade name PUREBRIGHT (registered trademark; hereinafter in the present specification, the same applies.) by NOF Corporation.

Further, JP-A No. 2003-137816 discloses a method of solubilizing paclitaxel or the like using the above copolymer. It is described that it is possible to dissolve a poorly water soluble drug such as paclitaxel at a high concentration by using the solubilizing method described in the above document.

However, in the solubilizing method using the above copolymer, since heating is needed, there are concerns regarding the deterioration of the drug. Further, since this solubilizing method requires a large amount of the copolymer in order to enhance the solubility, although the degree of solubility is enhanced, the diffusibility of the drug is lowered, and thus, it is difficult to improve the membrane permeability and bioabsorbability of the drug. Therefore, for obtaining a preparation for oral administration, which is most desirable from the viewpoint of QOL, the bioavailability is insufficient, and further improvement is needed.

SUMMARY OF INVENTION

Technical Problem

Accordingly, an object of the present invention is to provide a pharmaceutical composition including a poorly water soluble drug, the pharmaceutical composition having both good membrane permeability and good bioabsorbability property, and a method of producing the same; and a preparation for oral administration, which includes the pharmaceutical composition.

Solution to Problem

The present invention is described below.

[1] A pharmaceutical composition including drug-containing nanoparticles having an average particle diameter of from 10 nm to 150 nm, the pharmaceutical composition being obtained by mixing water with a poorly water soluble drug-containing, water miscible solution that contains a poorly water soluble drug having a water solubility of 50 μg/mL or less, a water soluble copolymer having a repeating unit represented by the following Formula (1), and a water miscible solvent:

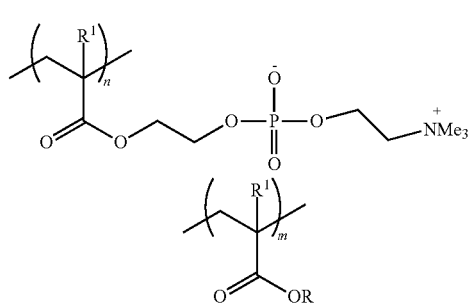

(1)

wherein, in Formula (1), n:m is within a range of from 0.25:0.75 to 0.95:0.05; R represents an alkyl group which may have a substituent; $R^1$ and $R^2$ each independently represent a hydrogen atom or a methyl group; and Me represents a methyl group.

[2] The pharmaceutical composition according to [1], including the water soluble copolymer in an amount of from 0.1 parts by mass to 3 parts by mass with respect to 1 part by mass of the poorly water soluble drug.

[3] The pharmaceutical composition according to [1] or [2], wherein the water miscible solvent is at least one water miscible solvent selected from the group consisting of ethanol, methanol, acetone, acetonitrile, and dimethyl sulfoxide.

[4] The pharmaceutical composition according to any of [1] to [3], wherein the content of the poorly water soluble drug is from 0.1% by mass to 10% by mass with respect to the total mass of the composition.

[5] The pharmaceutical composition according to any of [1] to [4], wherein the water soluble copolymer has an important average molecular weight of from 5000 to 1000000.

[6] The pharmaceutical composition according to any of [1] to [5], wherein the water soluble copolymer is a water soluble copolymer which is represented by the following Formula (2) and has a weight average molecular weight of 30000.

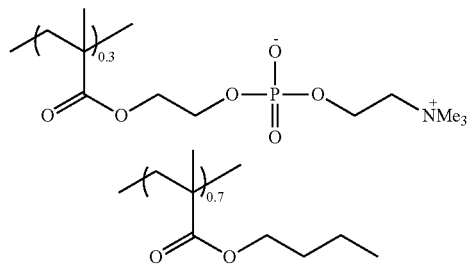

(2)

[7] A preparation for oral administration including the pharmaceutical composition according to any of [1] to [6].

[8] A method of producing the pharmaceutical composition according to [1], the method including mixing water with a poorly water soluble drug-containing, water miscible solution that contains a poorly water soluble drug having a water solubility of 50 μg/mL or less, a water soluble copolymer having a repeating unit represented by the following Formula (1), and a water miscible solvent:

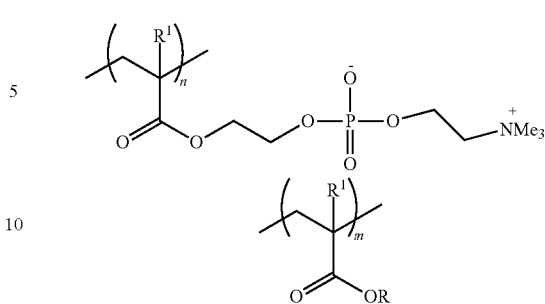

(1)

wherein, in Formula (1), n:m is within a range of from 0.25:0.75 to 0.95:0.05; R represents an alkyl group which may have a substituent; $R^1$ and $R^2$ each independently represent a hydrogen atom or a methyl group; and Me represents a methyl group.

[9] The method according to [8], further including mixing the poorly water soluble drug, the water soluble copolymer, and the water miscible solvent to prepare the poorly water soluble drug-containing, water miscible solution.

[10] The method according to [8] or [9], wherein the pharmaceutical composition includes the water soluble copolymer in an amount of from 0.1 parts by mass to 3 parts by mass with respect to 1 part by mass of the poorly water soluble drug.

[11] The method according to any of [8] to [9], wherein the mixing of water with the poorly water soluble drug-containing, water miscible is carried out at a proportion such that the amount of water is from 2 parts by mass to 50 parts by mass relative to 1 part by mass of the poorly water soluble drug-containing, water miscible solution.

[12] The method according to any of [8] to [11], wherein the water miscible solvent is at least one water miscible solvent selected from the group consisting of ethanol, methanol, acetone, acetonitrile, and dimethyl sulfoxide.

[13] A method of administration of a poorly water soluble drug, the method including administering the pharmaceutical composition according to any of [1] to [5] to a subject.

[14] The method administration of a poorly water soluble drug according to [13], wherein the administration is oral administration.

BEST MODE FOR CARRYING OUT THE INVENTION

The pharmaceutical composition of the present invention is a pharmaceutical composition including drug-containing nanoparticles having an average particle diameter of from 10 nm to 150 nm, and the pharmaceutical composition is obtained by mixing water with a poorly water soluble drug-containing, water miscible solution that contains a poorly water soluble drug having a water solubility of 50 μg/mL or less, a water soluble copolymer having a repeating unit represented by Formula (1) above, and a water miscible solvent.

According to the present invention, the poorly water soluble drug is prepared into a pharmaceutical composition which contains the poorly water soluble drug in the form of fine dispersion particles, so-called nanoparticles, and is obtained by mixing water with a poorly water soluble drug solution containing the poorly water soluble drug, a specified copolymer and a water miscible solvent, and thus, a pharmaceutical composition which has excellent membrane permeability and excellent bioabsorbable property can be produced. Further, since the pharmaceutical composition of the present invention has excellent membrane permeability and excellent bioabsorbable property, the pharmaceutical composition is suitably used as a preparation for oral administration.

Note that, the term "drug-containing particles" used in the present invention refers to dispersion particles containing a poorly water soluble drug as one of the constituent elements. Further, in this specification, the drug-containing particles may be referred to as "drug-containing nanoparticles" in some cases.

In this specification, the term "process" includes not only an independent process, but also a case which cannot be clearly distinguished from other process, as far as the predetermined action of the process is achieved.

Further, in this specification, a numerical range described by using the term "to" represents a range including numerical values described in front of and behind "to", as the minimum value and the maximum value.

Moreover, in the present invention, in the case of referring to an amount of a component in the composition, when plural substances corresponding to the component exist in the composition, the amount means the total amount of the plural substances existing in the composition, unless noted specifically otherwise.

Hereinafter, exemplary embodiments of the present invention are explained.

[1] Pharmaceutical Composition (1) Poorly Water Soluble Drug

The poorly water soluble drug according to the present invention is not limited as far as the poorly water soluble drug has a water solubility at 37° C. of 50 µg/mL or less. Further, from the viewpoint of adjusting the particle diameters of nanoparticles, it is preferable that the poorly water soluble drug in the present invention dissolves in the water miscible solvent described below in a proportion of 1% by mass or more at 25° C. Examples of such poorly water soluble drug include alkaloids (paclitaxel, docetaxel, camptothecin, etoposide, or the like), macrolides (erythromycin, clarithromycin, azithromycin, tacrolimus, or the like), statins (atorvastatin, simvastatin, or the like), azoles (itraconazole or the like), sulfonylureas (glibenclamide or the like), cyclic peptides (cyclosporin A or the like), polyenes (amphotericin B or the like), probucol, rifampicin, curcumin, carbamazepine, and fenofibrate; and among the above, paclitaxel, docetaxel, cyclosporin, and tacrolimus are particularly preferable. One kind of the poorly water soluble drugs may be used alone, or two or more kinds of them may be used in combination depending on the situation.

(2) Water Soluble Copolymer

The water soluble copolymer used in the present invention is a water soluble copolymer which is represented by Formula (1) above and is obtained by using 2-methacryloyloxy ethyl phosphoryl choline (MPC) and methacrylic acid or an ester thereof.

In Formula (1), n:m is within the range of from 0.25:0.75 to 0.95 to 0.05. From the viewpoint of dispersion stability of the drug-containing nanoparticles, n:m is preferably within the range of from 0.25:0.75 to 0.90 to 0.10, more preferably within the range of from 0.30:0.70 to 0.80:0.20, and particularly preferably, n:m is within the range of from 0.30:0.70 to 0.50:0.50.

R represents an alkyl group which may have a substituent. The alkyl group represented by R is preferably an alkyl group having from 1 to 18 carbon atoms, and more preferably an alkyl group having from 1 to 12 carbon atoms, from the viewpoint of affinity with the poorly water soluble drug. Further, the alkyl group represented by R may have one or more substituents such as an aryl group, an alkoxy group, an aryloxy group, a hydroxyl group, an amino group, or a carboxyl group. Specifically, the alkyl group represented by R is preferably a methyl group, an ethyl group, an n-propyl group, an n-butyl group, a t-butyl group, an n-hexyl group, a cyclohexyl group, a stearyl group, or a benzyl group, and particularly preferably an n-butyl group. $R^1$ and $R^2$ each independently represent a hydrogen atom or a methyl group, and Me represents a methyl group.

The weight average molecular weight of the water soluble copolymer in the present invention is preferably 5000 or more, and particularly preferably 10000 or more, from the viewpoint of dispersion stability of the drug-containing nanoparticles. Further, from the viewpoint of preventing the reduction in bioabsorbable property, the weight average molecular weight of the water soluble copolymer is preferably 1000000 or less, and particularly preferably 200000 or less.

In the present invention, from the viewpoints of the stability of the drug-containing nanoparticles and the absorption accelerating effect, PUREBRIGHT 50T (NOF Corporation) which is a compound in which n:m is 0.30:0.70 and R represents an n-butyl group in Formula (1) above and has a molecular weight of 30000 can be particularly preferably used as the water soluble copolymer.

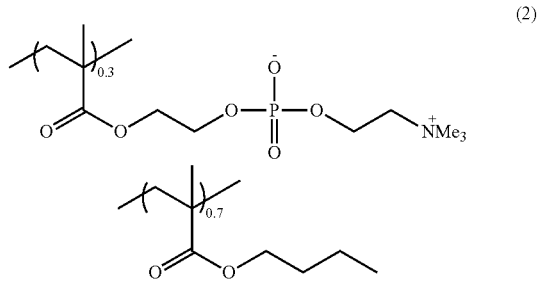

(2)

The water soluble copolymer in the present invention can be synthesized by a known method. For example, the water soluble copolymer can be obtained by reacting MPC and BMA at a specified proportion in a solvent, for example, in a mixed solvent of tetrahydrofuran and ethanol, in the presence of a polymerization initiator such as α,α'-azobis(isobutyronitrile) at a temperature of from 60° C. to 65° C. for a period of from 4 hours to 20 hours. Further, in the present invention, a commercially available product of the water soluble copolymer according to the present invention may be used. The synthesis methods are disclosed in JP-A No. 2003-137816 and the like.

(3) Water Miscible Solvent

The water miscible solvent in the pharmaceutical composition of the present invention is not particularly limited as far as the water miscible solvent is an organic solvent which can dissolve mutually with water in any proportion and is pharmaceutically acceptable, and for example, the water miscible solvent refers to an organic solvent having a degree of solubility with respect to water at 25° C. of 10% by mass or more. The degree of solubility of the water miscible solvent with respect to water is preferably 30% by mass or more, and more preferably 50% by mass or more, from the viewpoint of the stability of the obtained dispersion. Examples of such water miscible solvent include lower alkanols, for example, ($C_1$ to $C_3$) alkanols such as methanol, ethanol, or propanol; phenyl ($C_1$ to $C_3$) alkanols such as benzyl alkanol; lower ketones, for example, ($C_3$ to $C_4$) ketones such as acetone or ethyl methyl ketone; cyclic ethers such as dioxane or tetrahydrofuran; glycols, such as ethylene glycol, propylene glycol, or ethylene glycol monomethyl ether, and partially etherized products thereof; lower amides such as dimethyl formamide or diethyl formamide; acetic acid; dimethyl sulfoxide; pyridine; and acetonitrile. One kind of these water miscible solvent may be used alone, or two or more kinds of them may be used in combination. Among the above, the water miscible solvent is preferably ethanol, methanol, acetone, acetonitrile, or dimethyl sulfoxide, or a combination of two or more of them.

(4) Pharmaceutical Composition

The pharmaceutical composition of the present invention is a pharmaceutical composition including drug-containing nanoparticles having an average particle diameter of from 10 nm to 150 nm, and the pharmaceutical composition is obtained by mixing water with a poorly water soluble drug-containing, water miscible solution that contains a poorly water soluble drug, a water soluble copolymer, and a water miscible solvent. By mixing water with such a poorly water soluble drug-containing, water miscible solution, drug-containing nanoparticles which have suitable bioabsorbable property can be obtained without requiring a heating process and also without using an excess amount of water soluble copolymer.

The water soluble copolymer is effective in the dispersion stability of the drug-containing nanoparticles but, since the water soluble copolymer has a tendency of lowering the biomembrane permeability, it is especially important to set the compounding ratio of the poorly water soluble drug and the water soluble copolymer to a compounding ratio which further accelerates the bioabsorbable property. Accordingly, regarding the content ratio of the poorly water soluble drug and the water soluble copolymer in the poorly water soluble drug-containing, water miscible solution, the content of the water soluble copolymer is preferably from 0.1 parts by mass to 3 parts by mass, more preferably from 0.25 parts by mass to 2 parts by mass, and particularly preferably from 0.5 parts by mass to 1.5 parts by mass, relative to 1 part by mass of the poorly water soluble drug.

The content of the poorly water soluble drug in the poorly water soluble drug-containing, water miscible solution is preferably from 0.5% by mass to 10% by mass, and more preferably from 1% by mass to 5% by mass, from the viewpoint of easiness of adjusting the particle diameters of nanoparticles.

Further, the mixing ratio of the poorly water soluble drug-containing, water miscible solution and water is preferably such that the amount of water is from 2 parts by mass to 50 parts by mass, and more preferably from 5 parts by mass to 40 parts by mass, relative to 1 part by mass of the poorly water soluble drug-containing, water miscible solution, from the viewpoint of adjusting the particle diameter of the nanoparticle to be obtained to the desired particle diameter.

The drug-containing nanoparticles in the obtained pharmaceutical composition should be drug-containing nanoparticles having an average particle diameter of from 10 nm to 150 nm. When the average particle diameter exceeds 150 nm, the membrane permeability and the bioabsorbable property are insufficient. From the viewpoint of membrane permeability, the particle diameter of the nanoparticle is preferably from 10 nm to 100 nm, and particularly preferably from 10 nm to 50 nm. Note that, the term "average particle diameter of the drug-containing nanoparticles" used in the present invention means a median diameter determined by dynamic light scattering in water.

The particle diameter of the drug-containing nanoparticle can be measured with the use of a commercially available particle size distribution analyzer or the like.

Known examples of a method for measuring the particle size distribution include an optical microscopic method, a confocal laser scanning microscopic method, an electron microscopic method, an atomic force microscopic method, a static light scattering method, a laser diffraction method, a dynamic light scattering method, a centrifugal sedimentation method, an electric pulse measurement method, a chromatography method, and an ultrasonic attenuation method; and apparatuses based on the principles of the respective methods are commercially available.

As a method for measuring the particle diameter of the drug-containing nanoparticle in the present invention, it is preferable to apply a dynamic light scattering method in view of the particle diameter range and ease of measurement.

Examples of a commercially available measurement apparatus using dynamic light scattering include NANOTRAC UPA (Nikkiso Co., Ltd.), DYNAMIC LIGHT SCATTERING PARTICLE SIZE DISTRIBUTION ANALYZER LB-550 (HORIBA Ltd.), and FIBER-OPTICS PARTICLE SIZE ANALYZER FPAR-1000 (Otsuka Electronics Co., Ltd.).

The particle diameter of the drug-containing nanoparticle in the present invention is a value measured using NANOTRAC UPA (Nikkiso Co., Ltd.) and specifically, a value measured in a manner described below is adopted.

Namely, in the method for measuring the particle diameter, dilution is carried out with pure water such that the concentration of the poorly water soluble drug, which is included in a sample isolated from the pharmaceutical composition of the present invention, becomes 1% by mass, and measurement is carried out using a quartz cell. The particle diameter can be determined as a median diameter by setting the sample refractive index to 1.600 and the dispersion medium refractive index to 1.333 (pure water), and using the viscosity of pure water as the viscosity of the dispersion medium.

In the pharmaceutical composition of the present invention, regarding the particle diameter of the drug-containing nanoparticles, micronized drug-containing nanoparticles having an intended particle diameter of from 10 nm to 150 nm can be obtained based on factors such as agitation conditions (shearing force, temperature, and pressure) in the production method of the dispersion composition described below and the proportion of a poorly water soluble drug-containing, water miscible solution phase to a water phase, in addition to the factors due to the components contained in the composition.

The content of the poorly water soluble drug in the pharmaceutical composition of the present invention is preferably from 0.1% by mass to 10% by mass, and more preferably from 0.2% by mass to 10% by mass, with respect to the total mass of the composition, from the viewpoint of effective administration in an oral administration form or absorption of the drug; however, the content is not particularly limited.

[2] Method of Producing Pharmaceutical Composition

A method of producing the pharmaceutical composition of the present invention includes mixing water with a poorly water soluble drug-containing, water miscible solution that contains the above-described poorly water soluble drug, water soluble copolymer, and a water miscible solvent.

According to the production method in the present invention, it is possible to separate drug-containing nanoparticles which contain the poorly water soluble drug and have a specified average particle diameter.

In the mixing of water with the poorly water soluble drug-containing, water miscible solution, the conditions generally applied to mixing of solutions may be applied as they are, for example, a liquid may be added to another liquid, while stirring the another liquid under the temperature condition of from 4° C. to 50° C., preferably from 4° C. to 30° C. As to the mixing method, in order to adjust the particle diameter of the nanoparticle to the desired particle diameter, it is preferable to stir rapidly and uniformly, and it is preferable to add the poorly water soluble drug-containing, water miscible solution at a constant rate to water in a state of being stirred. Further, the mixing may be conducted by using a mixing apparatus suitable for separation of nanoparticles, for example, MRT (POWREX Corporation) or the like. The production method in the present invention makes it possible to minimize the compounding ratio of the water soluble copolymer to the poorly water soluble drug as compared with known methods.

As described above, the mixing of water with the poorly water soluble drug-containing, water miscible solution is preferably carried out at a ratio such that the amount of water is from 2 parts by mass to 50 parts by mass, and more preferably from 5 parts by mass to 40 parts by mass, relative to 1 part by mass of the poorly water soluble drug-containing, water miscible solution, from the viewpoint of adjusting the particle diameter of the nanoparticle to be obtained to the desired particle diameter. When this mixing is carried out more rapidly and uniformly, it is possible to make the particle diameter of the nanoparticle smaller.

The production method of the present invention may be a method which includes mixing the poorly water soluble drug, the water soluble copolymer, and the water miscible solvent, thereby preparing a poorly water soluble drug-containing, water miscible solution, to provide the poorly water soluble drug-containing, water miscible solution.

The method of preparing the poorly water soluble drug and the water miscible solvent is not particularly limited and, for example, as described above, it is preferable to mix at a proportion such that the content ratio of the water soluble copolymer becomes from 0.1 parts by mass to 3 parts by mass relative to 1 part by mass of the poorly water soluble drug, it is more preferable to mix at a proportion such that the content ratio of the water soluble copolymer becomes from 0.25 parts by mass to 2 parts by mass relative to 1 part by mass of the poorly water soluble drug, and it is particularly preferable that the proportion is such that the content ratio of the water soluble copolymer becomes from 0.5 parts by mass to 1.5 parts by mass relative to 1 part by mass of the poorly water soluble drug. Regarding other mixing conditions, the same conditions as those described above may be described.

Further, after mixing water with the poorly water soluble drug-containing, water miscible solution, the particle diameters of the dispersion particles in the dispersion liquid may be made uniform by using a known filtration method or the like. In this way, a pharmaceutical composition having a uniform particle diameter can be obtained. Further, after the formation of nanoparticles, a free drug or a free water miscible solvent which exists in water may be removed by using known ultrafiltration, dialysis, or the like.

Since the pharmaceutical composition of the present invention can improve the membrane permeability and bioabsorbable property of poorly water soluble drugs, the pharmaceutical composition of the present invention can be used for various purposes. For example, the pharmaceutical composition of the present invention may be particularly preferably used for a preparation for oral administration. Namely, the preparation for oral administration of the present invention contains the pharmaceutical composition described above. The content ratio of the pharmaceutical composition of the present invention in the preparation for oral administration is not particularly limited and can be determined according to the mode of the preparation for oral administration, the kind of the poorly water soluble drug, the age of the patient to be applied, and the like.

Furthermore, the pharmaceutical composition in the present invention may include an additive or additives which are generally used in pharmaceutical preparation, other than the poorly water soluble drug, the water soluble copolymer, and the water miscible solvent. Examples of such additives may include vehicles (mannitol, trehalose, lactose, cellulose derivatives, or the like), emulsification agents (sorbitan fatty acid esters, polyoxyethylene hydrogenated castor oil, polyglycerin fatty acid esters, sucrose fatty acid esters, or the like), and coating agents (poly methacrylic acid esters or polyvinyl pyrrolidone).

With respect to the preparation for oral administration, the pharmaceutical composition of the present invention in the form of a dispersion liquid may be administrated to a subject, or the pharmaceutical composition of the present invention may be administered to a subject after powderizing or granulating the pharmaceutical composition by a conventional method such as a spray dry method.

The present invention also includes a method of administration of a poorly water soluble drug. The method of administration of a poorly water soluble drug according to the present invention includes administering the pharmaceutical composition described above to a subject.

In the administration method of the present invention, a pharmaceutical composition which includes a poorly water soluble drug in the form of fine dispersion particles, so-called nanoparticles, and is obtained by mixing water with a poorly water soluble drug solution containing the poorly water soluble drug, a specified copolymer and a water miscible solvent, is administrated to subjects; and thus, the poorly water soluble drug can be administered with good membrane permeability and good bioabsorbable property. As a result, a higher treatment effect of the poorly water soluble drug can be expected.

In the administration method of the present invention, the administration mode is particularly preferably oral administration.

EXAMPLES

Hereinafter, the present invention will be described in detail with reference to Examples. However, it should be construed that the invention is by no means limited thereto. Note that, unless otherwise specifically stated, the term "parts" is based on mass.

Example 1

0.096 g of paclitaxel as a poorly water soluble drug, and 0.16 g of PUREBRIGHT 50T (NOF Corporation) as a water-soluble copolymer were dissolved in 4.544 mL of ethanol. This was rapidly mixed into 48 mL of ultrapure water being stirred, under an environment of 23° C., to separate nanoparticles of paclitaxel. Thereafter, ultrafiltration was carried out using ULTRAFILTER P2000 (manufactured by Advantec Toyo Kaisha, Ltd.; molecular weight cut off of 20000), and then ultrapure water was added to obtain dispersion liquid 1 containing paclitaxel in an amount of 3 mg/mL.

The average particle diameter of the thus obtained nanoparticles was measured using NANOTRAC UPA (manufactured by Nikkiso Co., Ltd.), and was found to be 26 nm. The formulation and particle diameter are shown in Table 1. Note that, in Table 1, the numeric values of ethanol, acetone, and ultrapure water represent the numeric values in mL (milliliters), and the numeric values of other components represent the numeric values in grams.

Examples 2 to 5 and Comparative Examples 1 to 4

Preparation of dispersion liquids 2 to 9 each containing a poorly water soluble drug in an amount of 3 mg/mL was conducted in the same manner as that in Example 1, except that the kinds or amounts of the poorly water soluble drug and other additive components were changed as shown in Table 1. The average particle diameters of the obtained dispersion liquids 2 to 9 were each measured in the same manner as that in Example 1. The results are shown in Table 1.

Note that, as the polyoxyethylene (C24) castor oil fatty acid ester, CREMOPHOR EL manufactured by BASF Corporation was used. As the PLGA (lactic acid.glycolic acid copolymer), PLGA manufactured by WAKO PURE Chemical Industries, Ltd. was used.

TABLE 1

|  |  | Example 1 Dispersion Liquid 1 | Example 2 Dispersion Liquid 2 | Example 3 Dispersion Liquid 3 | Example 4 Dispersion Liquid 4 | Example 5 Dispersion Liquid 5 |
|---|---|---|---|---|---|---|
| Solution | Paclitaxel (g) | 0.096 | 0.096 | 0.10 | 0.09 | |
|  | Cyclosporin A (g) | | | | | 0.08 |
|  | PUREBRIGHT 50T (g) | 0.16 | 0.48 | 0.10 | 0.045 | 0.08 |
|  | CREMOPHOR EL (g) | | | | | |
|  | PLGA (g) | | | | | |
|  | Ethanol (mL) | 4.544 | 4.224 | 7.3 | 8.865 | 1.84 |
|  | Acetone (mL) | | | | | |
| Aqueous Solution | PUREBRIGHT 50T (g) | | | | | |
|  | Ultrapure water (mL) | 48 | 48 | 50 | 100 | 40 |
| Evaluation | Particle diameter (nm) | 26 | 17 | 46 | 48 | 36 |

|  |  | Comparative Example 1 Dispersion Liquid 6 | Comparative Example 2 Dispersion Liquid 7 | Comparative Example 3 Dispersion Liquid 8 | Comparative Example 4 Dispersion Liquid 9 |
|---|---|---|---|---|---|
| Solution | Paclitaxel (g) | 0.08 | 0.096 | 0.09 | 0.09 |
|  | Cyclosporin A (g) | | | | |
|  | PUREBRIGHT 50T (g) | | | | |
|  | CREMOPHOR EL (g) | | | 0.09 | |
|  | PLGA (g) | | | | 0.09 |
|  | Ethanol (mL) | 3.92 | 4.704 | 7.32 | |
|  | Acetone (mL) | | | | 4.32 |
| Aqueous Solution | PUREBRIGHT 50T (g) | 0.08 | 0.16 | | |
|  | Ultrapure water (mL) | 39.92 | 47.84 | 94.5 | 94.5 |
| Evaluation | Particle diameter (nm) | 175 | 41 | precipitated | precipitated |

<Evaluation>

(1) Evaluation 1 of Intestinal Absorption—PAMPA—

With regard to the thus obtained dispersion liquids 1 to 4, dispersion liquids 6 and 7 as comparative examples, and a solubilized preparation (solubilized liquid), the effect of intestinal absorptivity was evaluated as follows, using an artificial lipid membrane PAMPA (manufactured by Nippon Becton Dickinson Company, Ltd.).

The test liquid was diluted with PBS buffer such that the concentration of the poorly water soluble drug was 100 μM, then the resulting liquid was added to each well of a donor plate, and an acceptor plate (in which PBS was added to each well) was set, followed by incubating at 37° C. for 2 hours, and then the concentration of paclitaxel in the well of the acceptor plate was quantified using HPLC. An apparent permeation coefficient Papp was calculated from the change in the obtained paclitaxel concentration. The experiment was conducted using, as comparator, a solubilized preparation which was obtained by solubilizing paclitaxel with CREMOPHOR:ethanol=1:1, and adjusting the concentration using PBS buffer. The results are shown in Table 2.

[Conditions for Quantification]
Column: CAPCELLPAK C18 UG120
(150 mm×3 mm, Shiseido Co., Ltd.)
Mobile phase: water/methanol
Flow rate: 0.5 mL/min
Wavelength: 230 nm (2) Evaluation 2 of Intestinal Absorption—In Vivo System—

With regard to the nanoparticle dispersions in Examples (dispersion liquids 3 and 4), an intestinal absorption test was carried out as follows, using male SD rats (7 weeks of age). As comparative substances, dispersion liquid 7 which was prepared by a conventional method (preparation of the dispersion liquid 7 is conducted by mixing only the poorly water soluble drug with ethanol, and then mixing the resulting liquid with an aqueous solution containing PUREBRIGHT), and a solubilized preparation, which was obtained by solubilizing paclitaxel with CREMOPHOR:ethanol=1:1, and adjusting the concentration with PBS buffer, were used.

The dispersion liquids 3 and 4, and the comparative preparations were each prepared into a medicinal liquid containing 3 mg/mL paclitaxel using purified water, and the obtained medicinal liquids were each orally administered at an amount of 30 mg/kg using a gastric tube. Samples of blood at 30 minutes, 1 hour, 2 hours, 4 hours, 6 hours, and 24 hours after the administration were drawn from the jugular vein. The blood samples were instantly subjected to centrifugal separation to collect blood serums. The obtained blood serums were each subjected to deproteinization and extraction in accordance with a conventional method, and then quantification was carried out using LC MS/MS. The maximum blood concentration (Cmax) and the area under the blood concentration (Area Under Concentration; AUC) are shown in Table 3.

TABLE 3

| | Example | | Comparative Example | |
|---|---|---|---|---|
| | Dispersion Liquid 3 | Dispersion Liquid 4 | Dispersion Liquid 7 | Solubilized Liquid |
| Cmax (ng/mL) | 1402 | 1533 | 441 | 172 |
| $AUC_{0 \to 24 \, hr}$ (ng · h/mL) | 7052 | 8846 | 2994 | 1553 |

As seen from the above, in the dispersion liquids 1 to 5, each of which was obtained by forming a poorly water soluble drug-containing, water miscible solution using paclitaxel or cyclosporin A together with PUREBRIGHT, and then mixing the resulting solution with ultrapure water, a dispersion liquid containing nano-sized dispersion molecules can be prepared easily with a smaller addition amount as compared with conventional techniques. Further, as seen from the results shown in Table 2 and Table 3, since these nanoparticle dispersion liquids were prepared using a small amount of dispersant in accordance with the method of the present invention, the pharmaceutical composition can exhibit excellent membrane permeability and excellent intestinal absorptivity. Accordingly, the pharmaceutical composition of the present invention has high membrane permeability and, in particular, the pharmaceutical composition of the present invention is useful for improving the intestinal absorptivity and bioavailability of poorly water soluble drugs.

The disclosure of Japanese Patent Application No. 2010-19723, filed on Jan. 29, 2010, is incorporated by reference herein in its entirety.

All publications, patent applications, and technical standards mentioned in this specification are herein incorporated by reference to the same extent as if such individual publication, patent application, or technical standard was specifically and individually indicated to be incorporated by reference.

TABLE 2

| | Example | | | | Comparative Example | | |
|---|---|---|---|---|---|---|---|
| | Dispersion Liquid 1 | Dispersion Liquid 2 | Dispersion Liquid 3 | Dispersion Liquid 4 | Dispersion Liquid 6 | Dispersion Liquid 7 | Solubilization Liquid |
| Papp (×10$^{-6}$ cm/sec) | 0.95 | 0.81 | 1.58 | 3.4 | 0.85 | 0.83 | 0.124 |

The invention claimed is:

1. A pharmaceutical composition comprising drug-containing nanoparticles having an average particle diameter of from 10 nm to 150 nm, the pharmaceutical composition being obtained by mixing:
   (a) water
   with
   (b) a water miscible solution which contains (i) a poorly water soluble drug having a water solubility of 50 μg/mL or less, (ii) a water miscible solvent, and (iii) a water soluble copolymer having a repeating unit of the following Formula (1),

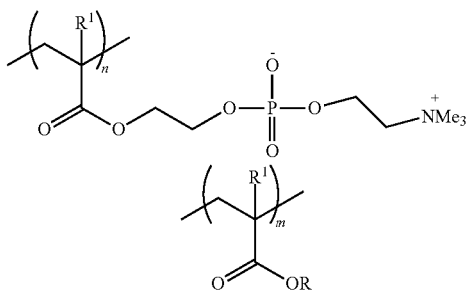

(1)

wherein, in Formula (1), n:m is within a range of from 0.25:0.75 to 0.95:0.05; R represents an alkyl group which may have a substituent; $R^1$ and $R^2$ each independently represents a hydrogen atom or a methyl group; and Me represents a methyl group, and the composition comprises the water soluble copolymer in an amount of from 0.5 parts by mass to 1.5 parts by mass with respect to 1 part by mass of the poorly water soluble drug.

2. The pharmaceutical composition according to claim 1, wherein the water miscible solvent is at least one water miscible solvent selected from the group consisting of ethanol, methanol, acetone, acetonitrile, and dimethyl sulfoxide.

3. The pharmaceutical composition according to claim 1, wherein the content of the poorly water soluble drug is from 0.1% by mass to 10% by mass with respect to the total mass of the composition.

4. The pharmaceutical composition according to claim 1, wherein the water soluble copolymer has a weight average molecular weight of from 5000 to 1000000.

5. The pharmaceutical composition according to claim 1, wherein the water soluble copolymer is a water soluble copolymer which is of the following Formula (2) and has a weight average molecular weight of 30000:

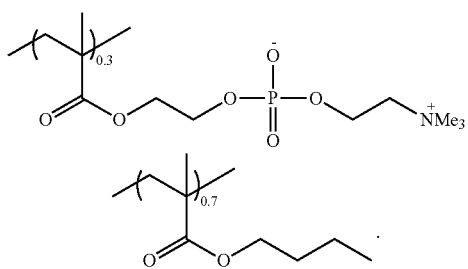

(2)

6. A preparation for oral administration, the preparation comprising the pharmaceutical composition according to claim 1.

7. A method of producing the pharmaceutical composition according to claim 1, the method comprising mixing:
(a) water
with
(b) a water miscible solution which contains (i) a poorly water soluble drug having a water solubility of 50 µg/mL or less, (ii) a water miscible solvent, and (iii) a water soluble copolymer having a repeating unit of the following Formula (1),

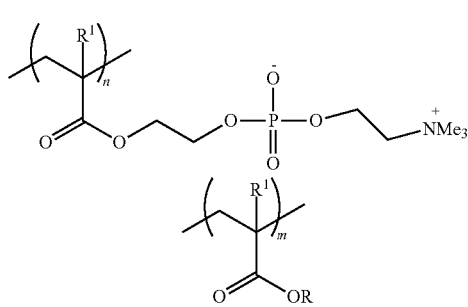

(1)

wherein, in Formula (1), n:m is within a range of from 0.25:0.75 to 0.95:0.05; R represents an alkyl group which may have a substituent; $R^1$ and $R^2$ each independently represents a hydrogen atom or a methyl group; and Me represents a methyl group, and the composition comprises the water soluble copolymer in an amount of from 0.5 parts by mass to 1.5 parts by mass with respect to 1 part by mass of the poorly water soluble drug.

8. The method according to claim 7, further comprising mixing the poorly water soluble drug, the water soluble copolymer, and the water miscible solvent to prepare the water miscible solution.

9. The method according to claim 7, wherein the mixing of (a) water with (b) the water miscible solution is carried out at a proportion such that the amount of water is from 2 parts by mass to 50 parts by mass relative to 1 part by mass of the water miscible solution.

10. The method according to claim 7, wherein the water miscible solvent is at least one water miscible solvent selected from the group consisting of ethanol, methanol, acetone, acetonitrile, and dimethyl sulfoxide.

11. A method of administration of a poorly water soluble drug, the method comprising administering the pharmaceutical composition according to claim 1 to a subject.

12. The method of administration of a poorly water soluble drug according to claim 11, wherein the administration is oral administration.

* * * * *